US00PP24195P2

(12) United States Plant Patent
Kordes

(10) Patent No.: US PP24,195 P2
(45) Date of Patent: Jan. 28, 2014

(54) SHRUB ROSE PLANT NAMED 'KORFIZZLEM'

(50) Latin Name: *Rosa hybrida*
Varietal Denomination: KORfizzlem

(75) Inventor: Tim-Hermann Kordes, Klein Offenseth-Sparrleshoop (DE)

(73) Assignee: W. Kordes' Söhne Rosenschulen GmbH & Co KG, Offenseth-Sparrleshoop (DE)

( * ) Notice: Subject to any disclaimer, the term of this patent is extended or adjusted under 35 U.S.C. 154(b) by 85 days.

(21) Appl. No.: 13/385,831

(22) Filed: Mar. 7, 2012

(51) Int. Cl.
*A01H 5/00* (2006.01)

(52) U.S. Cl.
USPC ..... Plt./104; Plt./101; Plt./102

(58) Field of Classification Search
USPC ..... Plt./101, 102, 104
See application file for complete search history.

*Primary Examiner* — Susan McCormick Ewoldt

(57) ABSTRACT

A new and distinct variety of rose with long lasting, novel yellow flowers, and attractive foliage with excellent disease resistance. It exhibits vigorous growth and an upright to bushy habit with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida*.

Variety denomination: The denomination of the new variety is 'KORfizzlem'. The new variety of rose plant of the present invention originated from a controlled crossing in a breeding program of two distinct parents during the summer of 2001. The crossing was between an 'un-named seedling' and an 'un-named seedling'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORfizzlem'.

CROSS REFERENCES AND FEDERAL R&D STATEMENT

There are no cross referenced or related applications. This variety was developed without the aid of any research grant.

SUMMARY OF THE INVENTION

The new rose plant may be distinguished from its seed parent, an 'un-named seedling', by the following combination of characteristics:

1. The flower size of 'KORfizzlem' is medium while the flower size of the seed parent is small.
2. The growth habit of 'KORfizzlem' is upright to bushy while the growth habit of the seed parent is upright.

The new rose plant may be distinguished from its pollen parent, an 'un-named seedling' by the following combination of characteristics:

1. The flower color of 'KORfizzlem' is yellow while the flower color of the pollen parent is soft apricot.
2. The petal count of 'KORfizzlem' is single while the petal count of the pollen parent is semi-double.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORfizzlem' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORfizzlem' was selected in May, 2002 from the seedling beds to be asexually propagated for further evaluation. The first asexual propagation of 'KORfizzlem' was done by budding to seedling understocks in July, 2002 at the inventor's nursery in Offenseth-Sparrieshoop, Germany.

This initial and other subsequent propagations conducted in controlled environments demonstrate that 'KORfizzlem' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORfizzlem'.

DETAILED BOTANICAL DESCRIPTION

The following is a description of 'KORfizzlem', as observed growing in October, 2011 in a nursery in Jackson County, Oreg. on plants of 3 years of age. Color references are made using The Royal Horticultural Society (London, England) Colour Chart, 2001 except where common terms of color are used.

For a comparison, several physical characteristics of the rose variety 'KORdwarul', a rose variety from the same inventor described and illustrated in U.S. Plant Pat. No. 19,746 and issued on Feb. 17, 2009 are compared to 'KORfizzlem' in Chart 1.

CHART 1

| Characteristic | 'KORfizzlem' | 'KORdwarul' |
|---|---|---|
| Fragrance: | None. | Light to moderate fragrance of spice and fruit |
| General tonality of open flower: | Yellow Group 13C. | Red-Purple Group 60B to 61B. |
| Average leaf size: | 55 mm long by 35 mm wide. | 95 mm long by 35 mm wide. |

Parents:

*Seed parent*.—An 'un-named seedling'.

*Pollen parent*.—An 'un-named seedling'.

Classification:

*Botanical classification*.—*Rosa hybrida* 'KORfizzlem'.

*Commercial classification*.—Shrub rose.

FLOWER AND FLOWER BUD

Blooming habit: Recurrent.

Flower bud:

*Size*.—Upon opening, 28 mm in length from base of receptacle to end of bud and 18 mm diameter at its widest point.

*Bud form*.—Long. Pointed ovoid.

*Bud color*.—As sepals first unfold, bud color is Yellow Group 14A with intonations of Red Group 44C. When ¼ open, the upper surface of petals is Yellow Group 7C, and the lower surface is Yellow Group 7C.

*Sepals*.—Color: Upper surface Yellow-Green Group 144D. Lower surface Yellow-Green Group 144B. Size: Average 20 mm long×8 mm wide. Shape: Weak foliaceous appendages on 1 to 2 of the five sepals. Apex: Apiculate. Base: Flat at union with receptacle. Quantity: Five. Surface texture: Upper side: Pubescent. Lower surface: With stipitate glands. Margins: With fine hairs and stipitate glands.

Receptacle:

*Surface*.—Smooth.

*Color*.—Yellow-Green Group 144A.

*Shape*.—Urn-shaped.

*Size*.—Average 20 mm long×8 mm wide.

Peduncle:

*Surface*.—With stipitate glands.

*Length*.—50 to 65 mm average length.

*Diameter*.—2 to 2.5 mm average diameter.

*Color*.—Yellow-Green Group 145A.

*Strength*.—Moderately strong.

*Borne*.—Multiple flower buds per stem, generally 1 to 5.

Flower bloom:

*Fragrance*.—None.

*Duration*.—On the plant 3 to 4 days. As a cut flower, 2 to 3 days. Senesced petals drop away cleanly.

*Size*.—Medium for a shrub rose. When open, the average flower diameter is 90 mm and the average flower height is 10 mm.

*Form*.—Shape of flower when viewed from the side: Upon opening, upper part: Flattened convex. Upon opening, lower part: Flattened convex. Open flower, upper part: Flat. Open flower, lower part: Flattened convex.

Color:

*Upon opening, petals*.—Outermost petals: Outer Side: Yellow Group 13B. Inner Side: Yellow Group 13B.

*Upon opening, basal petal spots*.—Basal petal spot, outermost petals: Outer Side: No petal spot. Inner Side: Yellow-Orange Group 14A.

*After opening, petals*.—Outermost petals: Outer Side: Yellow Group 10A. Inner Side: Yellow Group 10A.

*After opening, basal petal spots*.—Basal petal spot, outermost petals: Outer Side: No petal spot. Inner Side: Yellow Group 13A.

General tonality: On open flower Yellow Group 13C. No change in the general tonality at the end of the 3$^{rd}$ day. Afterwards, general tonality is Yellow Group 12D.

Petals:

*Petal count*.—Single.

*Average range*.—Approximately 5 petals under normal conditions.

*Petal reflex*.—Petals reflex slightly.

*Petal edge*.—Entire.

*Petal shape*.—Obtuse. Apex shape is pointed. Shape of base is rounded.

*Petal size*.—40 to 45 mm long by 40 to 50 mm wide.

*Thickness*.—Thick.

*Petal arrangement*.—Not formal.

Petaloids:

*Petaloid count*.—Average of 0 to 3 per flower.

*Petaloid size*.—Petaloids are 6 mm long and 3 mm wide on average.

*Petaloid color*.—Color of inner side is Yellow Group 13B. Color of outer side is Yellow Group 13B.

*Petaloid texture*.—Smooth.

*Margins*.—Undulated.

*Petaloid shape*.—Oblanceolate. Apex: Obtuse. Base: Attenuate.

Reproductive organs:

*Pistils*.—Approximately 20 to 25 present. Stigmas: Location: Inferior in position to anthers. Color: Green-Yellow Group 162C. Styles: Length: About 8 mm long. Color: Yellow-Green Group 145B with intonations of Red Group 45C.

*Stamens*.—Approximately 50 on average and regularly arranged. Anthers: Size: Average 2 mm long. Pollen: Generally present. Color: Greyed-Orange Group N167A. Filaments: Color: Yellow-Orange Group 14A. Length: 12 mm.

THE PLANT

Growth: Vigorous growth.

Plant habit: Upright to bushy habit. When grown as a budded field grown plant, the average plant height is 120 cm and the average plant width is 80 cm.

Stems:

*Stem color*.—Juvenile wood: Yellow-Green Group 146C. Mature wood: Yellow-Green Group 144A.

*Stem surface*.—Juvenile wood: Smooth. Mature wood: Smooth.

Prickles: Present.

*Incidence*.—Average of 8 to 10 per each 10 cm of stem.

*Size*.—Average length: 7 mm.

*Color*.—Immature prickles: Greyed-Purple Group 184A. Mature prickles: Yellow-Green Group 145C.
*Shape*.—Concave.
*Anthocyanin*.—Observed on upper surface of mature thorns, Greyed-Purple Group 184B.

Leaves and leaflets: Normally 7 leaflets on normal leaves in middle of the stem.
*Venation pattern*.—Pyramidal net pattern.
*Leaf size*.—Average of 55 mm long by 35 mm wide.
*Abundance*.—Average.
*Texture*.—Thick. Upper side of leaflet: Semi-Glossy and smooth. Under side of leaflet: Matte and smooth.
*Color, mature foliage*.—Upper Leaf Surface: Green Group 137A. Lower Leaf Surface: Green Group 138B.
*Color, juvenile foliage*.—Upper Leaf Surface: Green Group 137C. Lower Leaf Surface: Green Group 138B.

Stipules:
*Size*.—15 mm long, 8 mm from distal tip to distal tip.
*Stipule color*.—Yellow-Green Group 146B.
*Anthocyanin*.—Observed on center of upper side, color of Greyed-Red Group 182D.
*Margins*.—With stipitate glands.
*Shape*.—Apex: Apiculate. Base: Slightly winged.

Petiole:
*Length*.—Average 20 mm.
*Diameter*.—Average 2 mm.
*Petiole color*.—Yellow-Green Group 144A.
*Underneath*.—Smooth.
*Margins*.—With stipitate glands.
*Prickles*.—Limited numbers on underside.

Petiole rachis:
*Length*.—Average 20 mm.
*Diameter*.—Average 2 mm.
*Color*.—Yellow-Green Group 144A.
*Margins*.—With stipitate glands.
*Anthocyanin*.—Observed on upper surface of at point of leaf attachment, Color of Greyed-Purple Group 184B.
*Prickles*.—A few small prickles underneath.
*Stipitate glands*.—Lacking.

Leaflets:
*Size*.—Average size of the terminal leaflet is 50 mm long by 30 mm wide.
*Shape*.—Ovate. Base: Obtuse. Apex: Acute.
*Margins*.—Finely serrated.
*Surface*.—Upper: Semi-glossy. Lower: Matte.
*Texture*.—Smooth.
*Arrangement*.—Odd pinnate.
*Venation*.—Reticulate.

Hips/seed formation: None observed.

Winter hardiness: To date, the variety has been grown successfully in USDA Zones 5 to 9.

Disease resistance: Excellent resistance to Powdery mildew (*Sphaerotheca pannosa*), blackspot (*Diplocarpon rosae*), rust (*Phragmidium* sp.), and Botrytis (*Botrytis cinerea*) diseases under normal growing conditions.

I claim:

1. A new and distinct variety of rose plant, as described and illustrated herein.

* * * * *

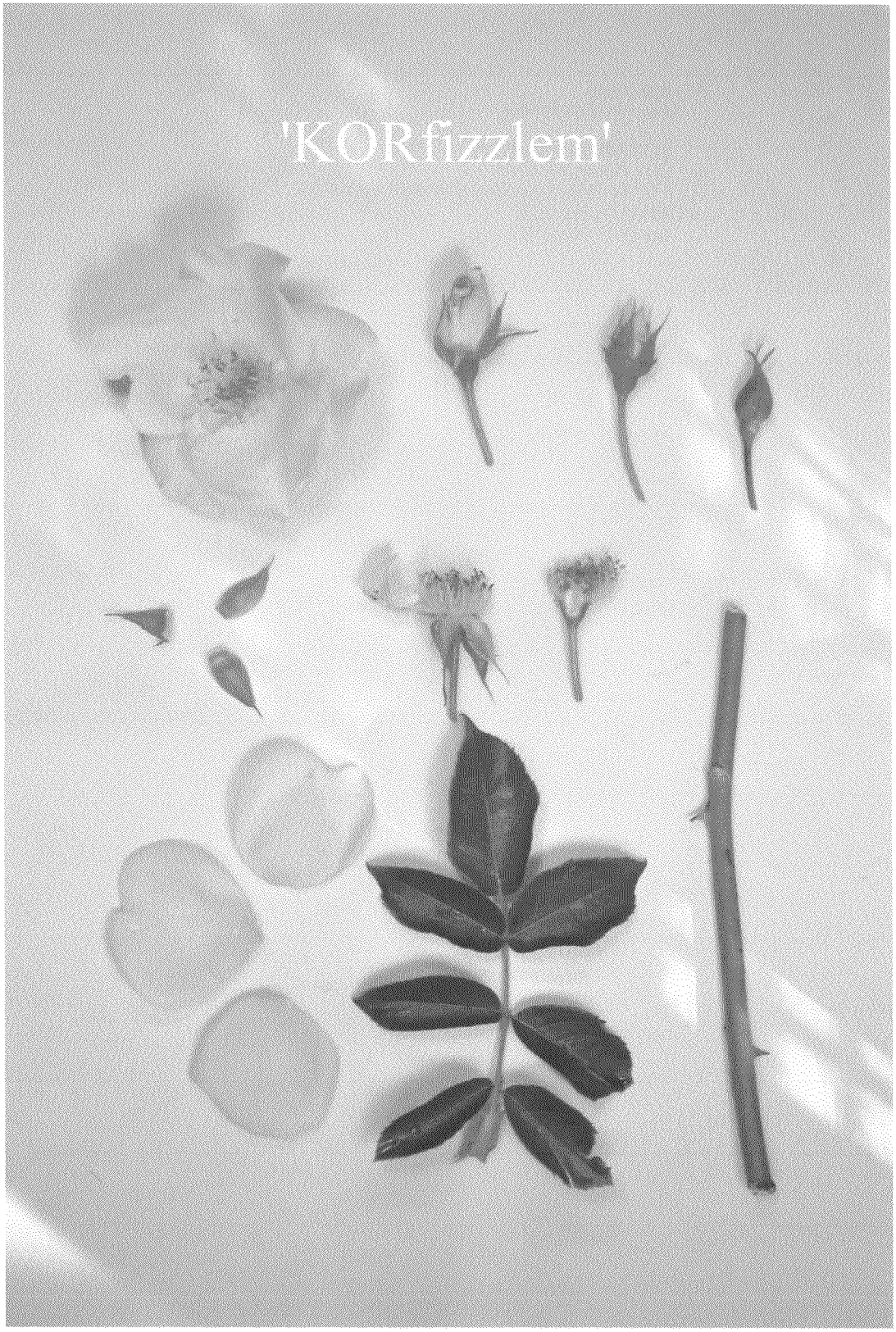
'KORfizzlem'